US012011712B2

(12) United States Patent
Hsu et al.

(10) Patent No.: US 12,011,712 B2
(45) Date of Patent: Jun. 18, 2024

(54) HIGH-EFFICIENCY SINGLE-CELL COLLECTION METHOD

(71) Applicant: National Health Research Institutes, Miaoli County (TW)

(72) Inventors: Chia-Hsien Hsu, Miaoli County (TW); Chuan-Feng Yeh, Miaoli County (TW)

(73) Assignee: NATIONAL HEALTH RESEARCH INSTITUTES, Zhunan Town (TW)

( * ) Notice: Subject to any disclaimer, the term of this patent is extended or adjusted under 35 U.S.C. 154(b) by 156 days.

(21) Appl. No.: 17/523,542

(22) Filed: Nov. 10, 2021

(65) Prior Publication Data

US 2022/0143595 A1    May 12, 2022

Related U.S. Application Data

(60) Provisional application No. 63/111,686, filed on Nov. 10, 2020.

(51) Int. Cl.
*B01L 3/00* (2006.01)
*B01L 3/02* (2006.01)
*C12N 1/02* (2006.01)

(52) U.S. Cl.
CPC ........... *B01L 3/0275* (2013.01); *B01L 3/0217* (2013.01); *C12N 1/02* (2013.01); *B01L 2300/0832* (2013.01); *B01L 2300/0858* (2013.01); *B01L 2300/12* (2013.01)

(58) Field of Classification Search
CPC ................ B01L 3/0275; B01L 3/0217; B01L 2300/0832; B01L 2300/0858; B01L 2300/12; C12N 1/02; B01N 3/0275; B01N 3/0217; B01N 2300/0832; B01N 2300/0858; B01N 2300/12
See application file for complete search history.

(56) References Cited

U.S. PATENT DOCUMENTS

| 6,723,289 | B2 * | 4/2004 | Iheme | B01L 3/0275 |
| | | | | 73/864.11 |
| 2006/0172433 | A1 * | 8/2006 | Motadel | B01L 3/0241 |
| | | | | 436/180 |

(Continued)

FOREIGN PATENT DOCUMENTS

| WO | WO-2017110005 | A1 * | 6/2017 | |
| WO | WO-2020131072 | A1 * | 6/2020 | ............ B01L 3/0275 |

OTHER PUBLICATIONS

WIPO English Machine Translation of WO2017/110005 to Ito (Year: 2017).*

*Primary Examiner* — Jill A Warden
*Assistant Examiner* — Michael Stanley Gzybowski
(74) *Attorney, Agent, or Firm* — MUNCY, GEISSLER, OLDS & LOWE, PC (57) ABSTRACT

This invention provides a high-efficient single-cell collection method using a specially designed collection well and collection pipet tip for particle/cell collection from the collection well. The structures of the collection well and pipet tip eliminate fluidic dead volume in the collection, resulting in all (or most) of the particles/cells can be brought into the collection pipette tip with the flow. The advantages of this invention in cell manipulation include high cell collection efficiency, low cell damage and easy operation procedure.

4 Claims, 9 Drawing Sheets
(1 of 9 Drawing Sheet(s) Filed in Color)

(56) References Cited

U.S. PATENT DOCUMENTS

| | | | |
|---|---|---|---|
| 2010/0248995 A1* | 9/2010 | Kensy | B01F 31/22 |
| | | | 506/39 |
| 2015/0072405 A1* | 3/2015 | Ito | B01L 3/502761 |
| | | | 422/68.1 |
| 2022/0001376 A1* | 1/2022 | Kinney | B01L 3/5635 |

* cited by examiner

Introducing a liquid containing a plurality of single-cell into a collection well and locating the plurality of single-cell at the bottom of the collection well.

Inserting a collection pipet tip into the collection well.

Giving a suction to draw the liquid with the plurality of single-cell into the collection pipet tip.

|  | Few residue | Completely removed | Collection efficiency % |
|---|---|---|---|
| Micro-wells chip (80 wells) | 44 wells | 36 wells | 45% |
| Flower-wells chip (80 wells) | 0 wells | 80 wells | 100% |

Fig. 4C

HIGH-EFFICIENCY SINGLE-CELL COLLECTION METHOD

CROSS REFERENCE TO RELATED APPLICATIONS

This application claims priority of U.S. Provisional Application No. 63/111,686 filed on 10 Nov. 2020 under 35 U.S.C. § 119(e), the entire contents of all of which are hereby incorporated by reference.

BACKGROUND OF THE INVENTION

Technical Field of the Invention

The present disclosure relates to the molecular biology field; more particularly, it relates to a high-efficiency single-cell collecting method for gently capturing a single cell without affecting the cell morphology.

Background

Single-cell analysis can reveal crucial clues from rare cells, which is essential for understanding complicated biological regulation within heterogeneous populations. Recently, the advances of cell handling and sequencing technology have allowed the analysis of single cell genomic/transcriptomic using commercialized systems, including lox genomic system, Cellsearch system and Fluidigm C I. Such systems can high throughput provide single cell-level genomic/transcriptomic information to discover novel biological mechanisms and develop new therapeutic strategies for treating diseases. Basically, single-cell analysis has been widely used in various biological fields and has the opportunity to be applied to clinical diagnosis, for example, analyzing circulating tumor cells isolated from peripheral blood of cancer patients.

However, the size of a single cell is only 10-20 μm, which makes a single-cell operation very difficult. It also emphasizes the need of special methods or devices to collect a single cell. The current single-cell operation methods, such as using micromanipulator, flow cytometer, single cell pipette, and filter, are still limited by the low efficiency, high shear stress, high cost and other issues. For example, by using filter to collect a single cell, the cells are susceptible to structural squeezing and fluid shearing forces. On the other hand, although flow cytometer is highly efficient in collecting single cell, the cells also are encountering the risks of being damaged by the shearing force of laser and fluid and it has higher costs. There is an urgent need of a single-cell collecting method with high-efficiency for genotyping and phenotype analysis of a single cell.

Therefore, the present invention provides a high-efficiency single-cell collecting method, comprising using a collection well and a collection pipet tip with novel structure to reduce the influence of boundary effect on the fluid in the collection well, thereby enabling all (or most) of the particles/cells in the collection well to be driven by the fluid and collected inside of the collection pipet tip. By these means, the purposes of low shear stress, fast and effective collection can be achieved. In addition, the present invention can be manually operated with a general pipet, reducing the cost of purchasing and maintaining equipment.

SUMMARY OF INVENTION

In one aspect, the present invention provides a high-efficiency single-cell collecting method, comprising introducing a liquid containing a plurality of single-cell into a collection well and locating the plurality of single-cell at the bottom of the collection well, inserting a collection pipet tip into the collection well, and giving a suction to draw the liquid with the plurality of single-cell into the collection pipet tip, wherein a gap distance of x is created between the pinpoint of the collection pipet tip and the bottom of the collection well while inserting the collection pipet tip into the collection well, and x is in a range of 10-500 μm.

The method presented in this disclosure provides a novel mean for capturing or collecting a single cell or a few cells in a quick and efficient way. Besides providing high efficiency, the method also has the advantages of high performance and low cost. It causes low cell damage and can be used with general optical microscopes to obtain high-content cell images for multi-oriented single-cell analysis. And the present invention can be operated manually with general pipet, so it does not require high equipment costs.

In one embodiment, the collection pipet tip and the collection well are made of polystyrene (PS), polyethylene (PE), poly(methyl methacrylate) (PMMA), polycarbonate (PC), cyclic olefin copolymer (COC), polydimethylsiloxane (PDMS) or liquid silicone rubber (LSR).

In one embodiment, the collection pipet tip is a pipet tip with a structure of at least three arc-shaped protrusions, wherein the collection pipet tip further comprises an outer wall disposed around the pinpoint.

In one embodiment, there is a height gap between the outer wall and the collection pipet tip.

In one embodiment, the collection well is a well with a structure of at least three arc-shaped protrusions.

In another preferred embodiment, the bottom of the collection well is smaller than the opening of the collection well and the walls of the collection well have a curve.

In one embodiment, the collection well and the collection pipet tip have the same number of the arc-shaped protrusion.

In one embodiment, the collection well and the collection pipet tip have a flower-shaped structure, four arc-shaped protrusions.

In one embodiment, the suction is provided by a general pipet.

Single-cell analysis is to identify the differences between individual cells in the entire population and help understand the heterogeneity and behavior of the population. An analysis of cell population only considers average attributes but cannot identify small and critical changes between individual cells of a sample. These reasons emphasize the importance of how to isolate and obtain single cells and also highlight the value of the present invention being easily operated and portable.

Therefore, in another aspect, the present invention can be extended to different applications, such as portable chip design, single cell operation, immunology, cancer and stem cell research, disease diagnosis and drug development, etc. For example, 1) stem cell/cancer cell heterogeneity analysis; 2) establishment of a single cell line; 3) monoclonal antibody drug development; 4) single cell related research (nucleic acid sequencing, protein analysis and single cell culture); 5) concentration of cell samples/biological particles; 6) analysis and experiment of very few cells (such as circulating tumor cells).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A-1D show the structure of the collection pipet tip and the collection well.

FIG. 3A-3C show the efficiency comparison of the single-cell collection in wells with different structures.

FIG. 4A-4C show the comparison of the collection efficiency between general micro-wells and the present collection well.

DETAILED DESCRIPTION OF THE INVENTION

Other features and advantages of the present invention will be further exemplified and described in the following examples, which are intended to be illustrative only and not to limit the scope of the invention.

Unless defined otherwise, all technical and scientific terms used herein have the same meaning as commonly understood by a person skilled in the art to which this invention belongs.

As used herein, the term of "flower-shaped" in the present disclosure is used to describe a structure of four arc-shaped protrusions.

EXAMPLES

The other characteristics and advantages of the present invention are further illustrated and described in the following examples. The examples described herein are using for illustrations, not for limitations of the invention.

The practice of the present invention will employ technologies comprising conventional techniques of cell biology and cell culture, which are within the ordinary skills of the art. Such techniques are explained fully in the literature

Example 1

The Structural Design of the Collection Pipet Tip and the Collection Well

As shown in FIG. 1A-1D, the collection pipet tip 10 is a pipet tip with a structure of four arc-shaped protrusions and an outer wall 101 around the pinpoint 102. And the collection well 11 is a well with a structure of four arc-shaped protrusions.

Figure 1A:
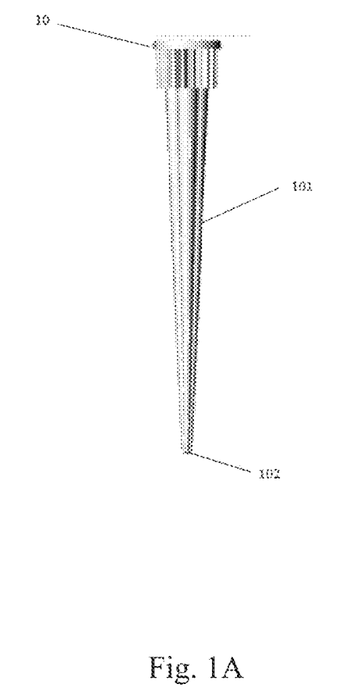
FIG. 1A shows the side view of the collection pipet tip.
Figure 1B:
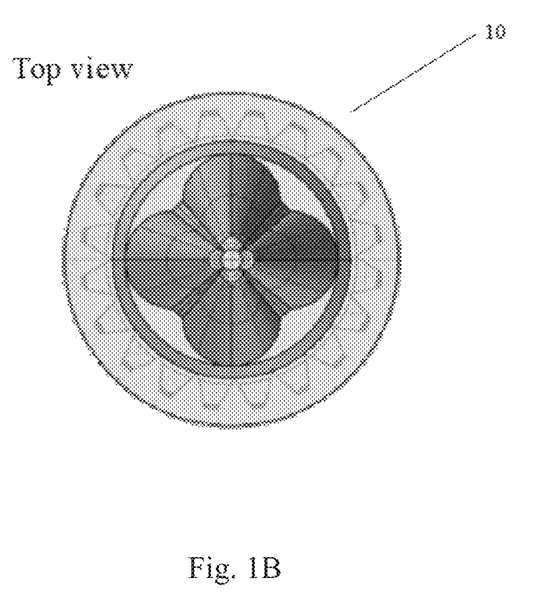
FIG. 1B shows the top view of the collection pipet tip.
Figure 1C:
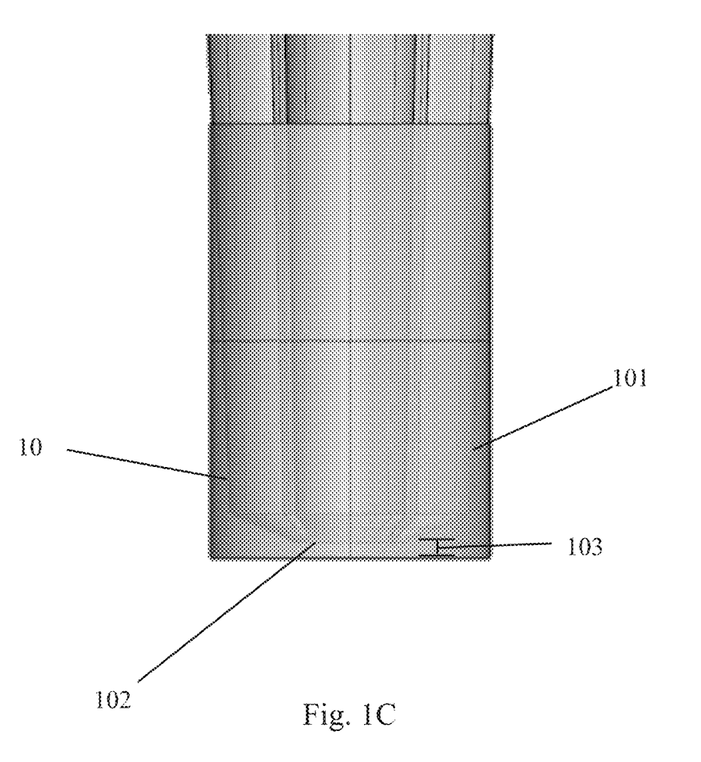
FIG. 1C exhibits the closer side view of the pinpoint of the collection pipet tip.

As illustrated in FIG. 1C, the collection pipet tip 10 has an outer wall 101 around pinpoint 102 of the collection pipet tip 10, and there is a height gap 103 between the outer wall 101 and the collection pipet tip 10. On the other hand, referring to FIG. 1D, the bottom 111 of the collection well 11 is smaller than the opening 112 of the collection well 11. When the collection pipet tip 10 is inserted into the collection well 11, the collection pipet tip 10 will not touch the bottom of the collection well 11 because of the wall of the collection well 11 having a curve. As a result, there is a gap distance 104 between them to prevent the collection pipet tip 10 from touching the bottom 111 of the collection well 11, wherein the gap distance is in a range of 10-500 μm.

Figure 1D:
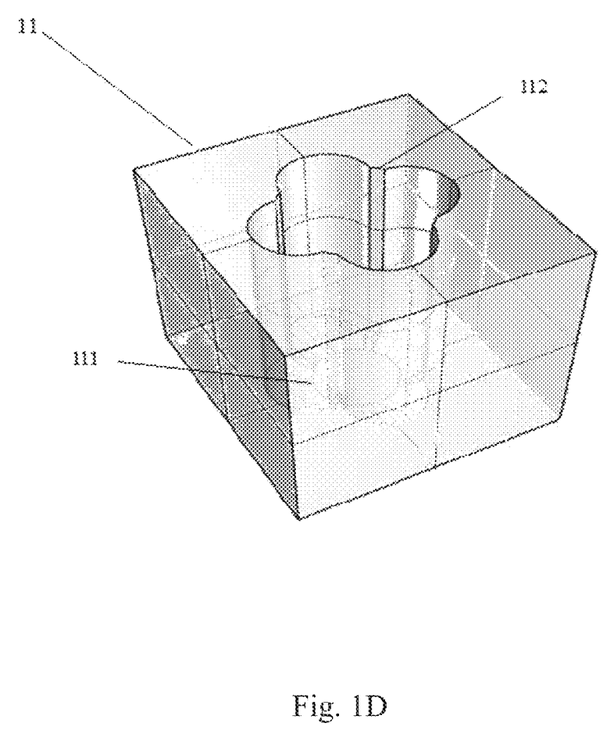
FIG. 1D is a perspective drawing showing the structure of the collection well.

Therefore, when the liquid containing particles/cells in the collection well 11 is sucked by the collection pipet tip 10, the pinpoint 102 of the collection pipet tip 10 has a certain distance from the bottom 111 of the collection well 11 and the particles/cells in the liquid are guided by the structure to the bottom 111 of the collection well 11 which is also under the projection of the pinpoint 102 of the collection pipet tip 10.

By these three-dimensional structure design of the collection well 11 and the collection pipet tip 10, the influence of the boundary effect on the fluid in the collection well 11 is reduced, thereby enabling all (or most) of the particles/cells in the collection well 11 to be driven by the fluid and collected inside of the collection pipet tip 10. The shear stress caused by fluid suction is reduced, which also lowers the chances of damaging the morphology of the single cells.

Example 2

Single Cell Isolation Methodology

Figure 2:
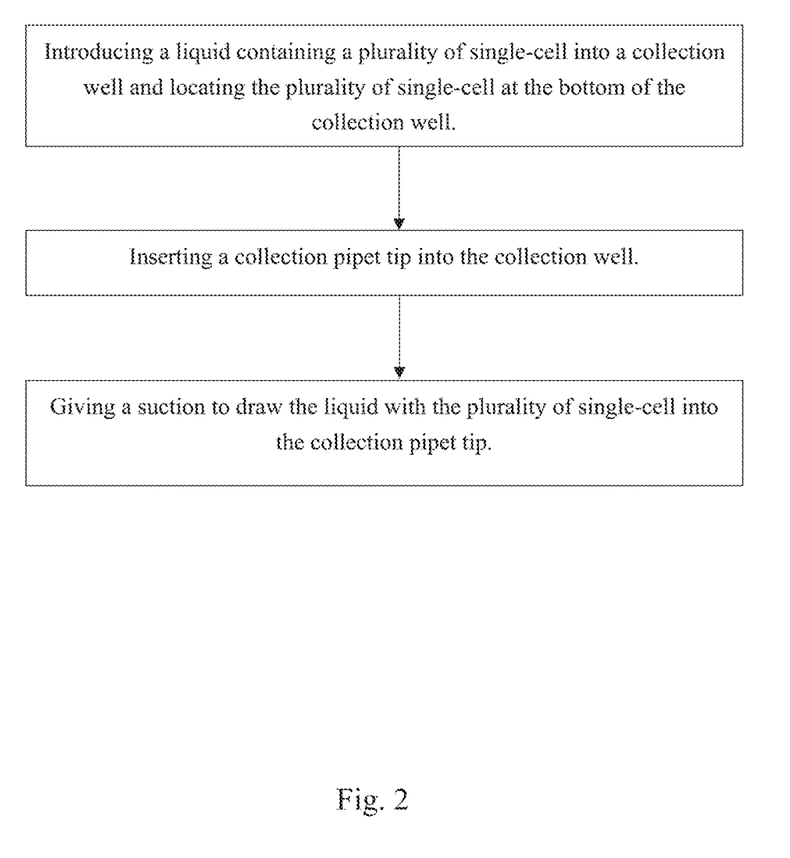
FIG. 2 depicts the single cell isolation flow chart.

As shown in FIG. 2, the single-cell collection method of the present invention is simple but efficient. First of all, introducing a liquid containing a plurality of desired single-cell or single-particle into the collection well. Second of all, putting the collection pipet tip on a general pipet and inserting the collection pipet tip into the collection well. With the special designed structure of the collection well, the pinpoint of the collection pipet tip has a distance gap from the bottom of the collection well, meaning that the collection pipet tip is not touching the bottom of the collection well and has a space allowing the flow rate of the liquid to change during the suction. Third of all, giving a suction provided by the pipet to draw the liquid into the collection pipet tip. Because of these structures and the gap distance, the flow rate of the liquid in the collection well or the collection pipet tip during the suction operation is increased. And during the suction, the direction of the fluid is from the outer wall side through the bottom to the collection tip, so that all (or most) of the particles/cells in the collection well is brought into the collection pipet tip to achieve the efficient collection.

Example 3

Figure 3A:
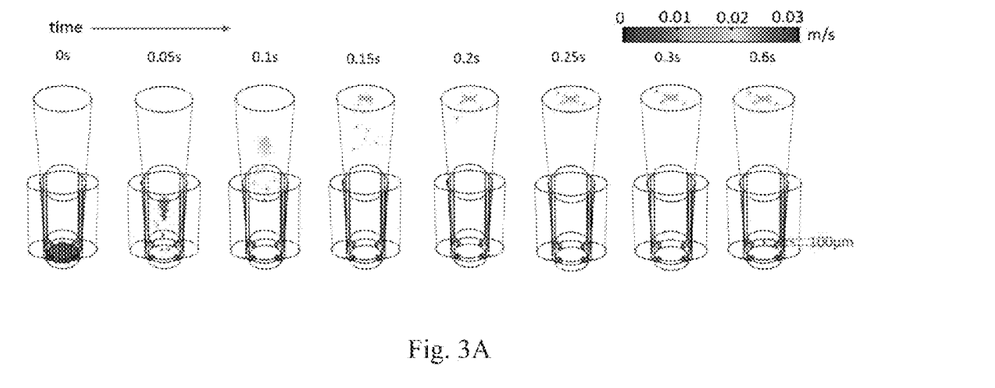
FIG. 3A exhibits the particle movement traces of 100 μm of the distance between the bottom and tip edge in the flower-shaped well.
Figure 3B:
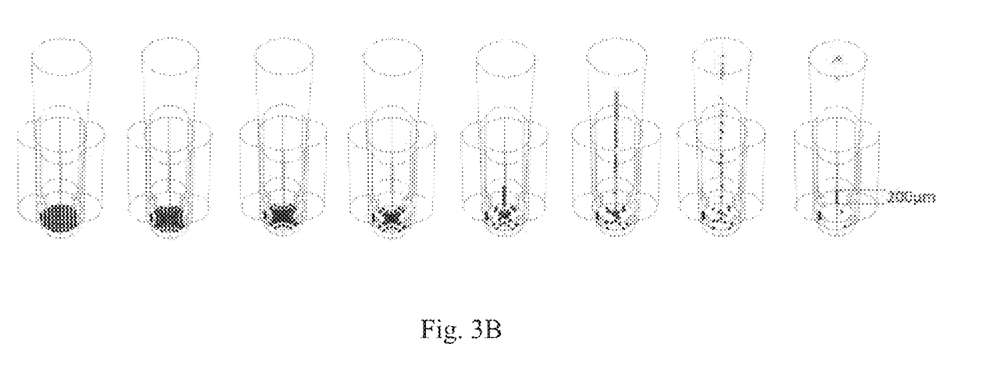
FIG. 3B shows the particle movement traces of 200 μm of the distance between the bottom and tip edge in the flower-shaped well.
Figure 3C:
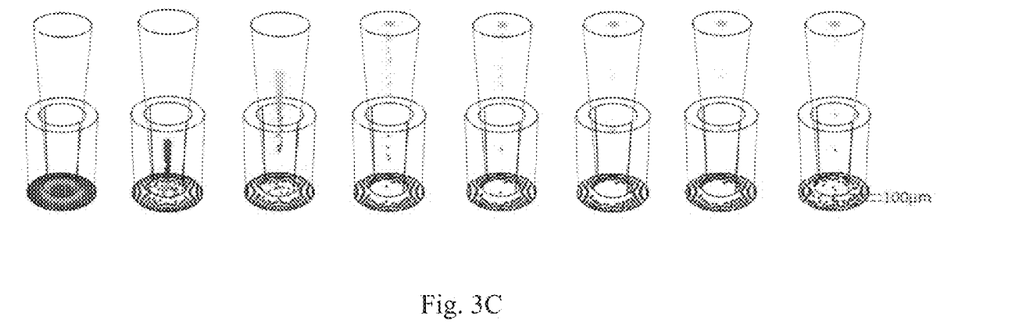
FIG. 3C depicts the particle movement traces of 100 μm of the distance between the bottom and tip edge in the general micro-well.

The efficiency of the Collection Well and the Collection Pipet with Floral Shaped Pinpoint To deep understanding of how the collection well and the collection pipet tip of the present invention affect particle's/cell's moving traces inside of wells during sipping liquid, a model for particle simulation using COMSOL Multiphysics® Modeling Software is constructed. The particle moving traces of 100 μm and 200 μm distances, which are the gap distance between the edge of the micro-tip and the well's bottom of flower-shaped wells, are compared. As shown in FIG. 3A, 100 μm of the gap in the flower-shaped well can allow all of the particles to move inside the micro-tip within 0.15 seconds. If the gap distance is increased to 200 μm, a few particles retain reside on the well bottom until 0.6 seconds (FIG. 3B). Therefore, the gap distance between tip and well bottom is a critical parameter, which affects particle movement speed. The particles moving traces in the general round-shape vertical sidewall of micro-wells at a gap distance of 100 μm are also simulated. The results demonstrated that some particles remain at the bottom around the sidewall circle of the well since the dead volume affects particle's moving speed (FIG. 3C).

These results suggest that the well with arc-shaped protrusions has a better efficiency of single-cell collection than the general round-shape well.

Example 4

Figure 4A:
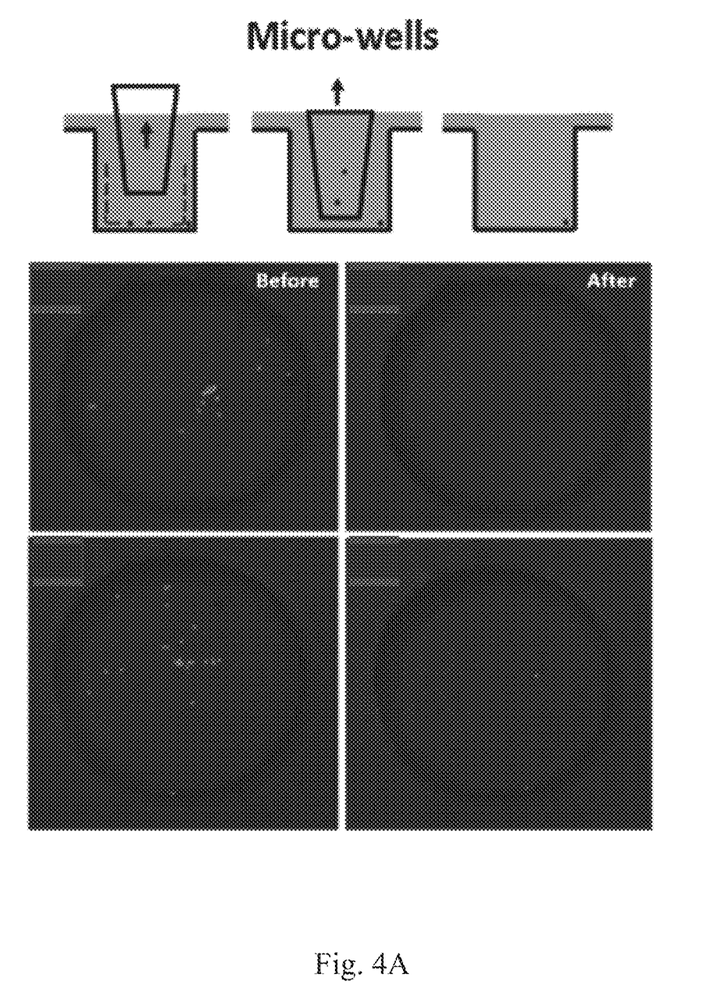
FIG. 4A shows the collection results by using the general micro-wells.
Figure 4B:
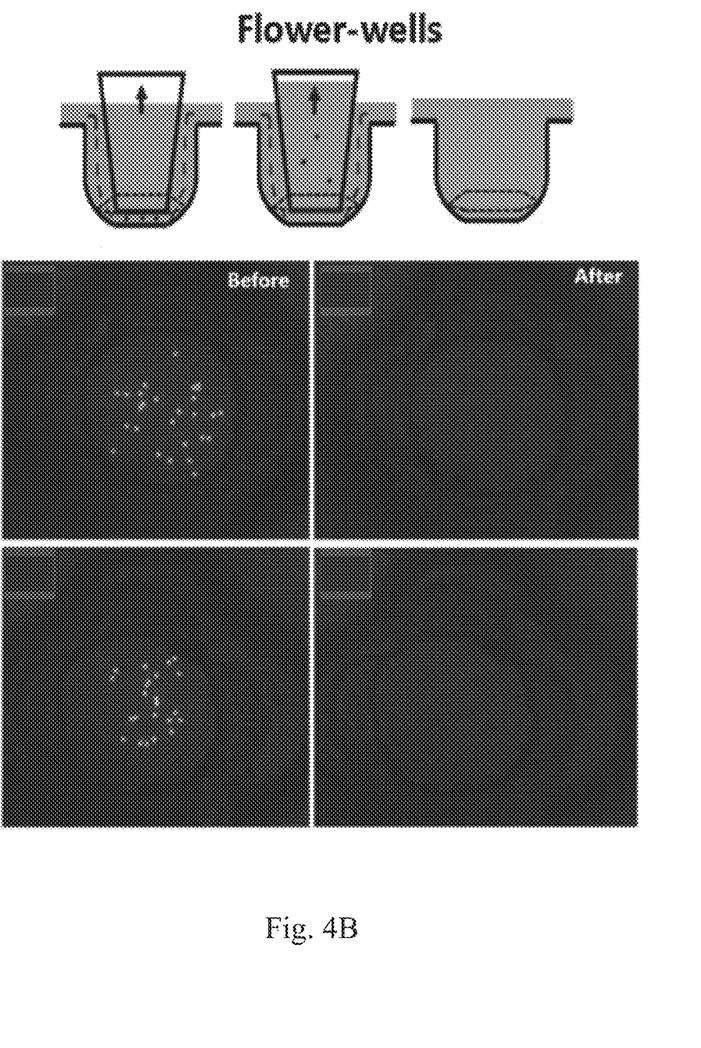
FIG. 4B shows the collection results by using the flower-shaped wells.
Figure 4C:
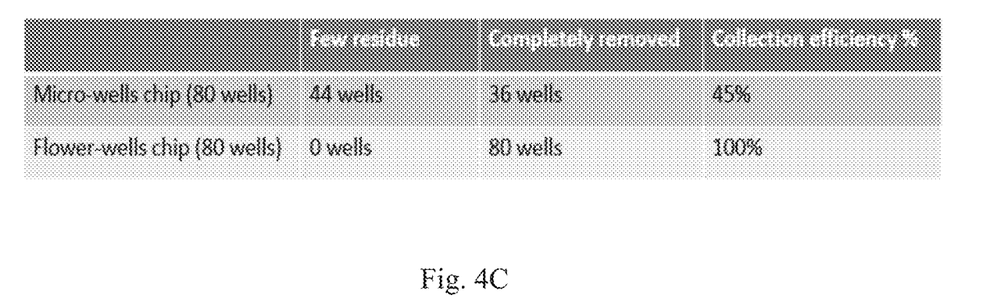
FIG. 4C demonstrates the efficiency comparison between the general micro-wells and the flower-shaped wells

The Comparison of the Collection Efficiency Between General Micro-Wells and the Present Collection Well General micro-well present dead volume near the sidewall and bottom, which is affected by the boundary effect to decrease the flow rate, the area is unable to push particles during absorbing liquid so that particles residue inside a well. Designed collection-wells with flower-shape and the curves of the sidewall, this allows guiding the streamline of flow in the well during liquid absorption to eliminate dead volume. The schematic diagram shows the side view of micro-wells, which retain particle residue (FIG. 4A), but flower-shaped well, which allows guiding the flow streamline in the well during liquid absorption to eliminate dead volume in (FIG. 4B). The particle collection-efficiency of the flower-shaped well is achieving to 100%, which is significantly higher than micro-well 45% (FIG. 4C).

The above comparisons show that the flower-shaped well with a certain curve near the bottom of the well can guide the flow streamline of the liquid with particles to be well absorbed by the pipet tip and decrease the residue left inside the well.

The invention claimed is:

1. A high-efficiency single cells collecting method, comprising:
   introducing a liquid containing one or more single cells into a collection well and locating each of the one or more single cells at a bottom of the collection well;
   inserting a collection pipet tip into the collection well; and
   applying suction to draw the liquid together with the one or more single cells into the collection pipet tip,
   wherein the collection pipet tip has a structure comprising at least three arc-shaped protrusions extending from an outer wall surface of the collection pipet tip, the collection well has a structure of at least three arc-shaped protrusions extending into an inner wall surface of the collection well, and a gap distance of x is created between a pinpoint of the collection pipet tip and the bottom of the collection well after inserting the collection pipet tip into the collection well, and wherein x is in a range of 10-500 um.

2. The method of claim 1, wherein the bottom of the collection well is smaller than a top opening of the collection well and bottom portions of the inner wall surface of the collection well have a curved shape.

3. The method of claim 1, wherein the inner wall surface of the collection well and the outer wall surface of the collection pipet tip have the same number of the arc-shaped protrusions.

4. The method of claim 1, wherein the collection well and the collection pipet tip are made of polystyrene (PS), polyethylene (PE), poly (methyl methacrylate) (PMMA), polycarbonate (PC), cyclic olefin copolymer (COC), polydimethylsiloxane (PDMS) or liquid silicone rubber (LSR).

* * * * *